United States Patent
Hansen et al.

(10) Patent No.: US 10,271,553 B2
(45) Date of Patent: Apr. 30, 2019

(54) SPOT-ON ACTIVE SUBSTANCE FORMULATION

(71) Applicant: Evergreen Animal Health, LLC, Gretna, NE (US)

(72) Inventors: Olaf Hansen, Leverkusen (DE); Rudy Thoma, Michendorf (DE)

(73) Assignee: Evergreen Animal Health, LLC, Gretna, NE (US)

( * ) Notice: Subject to any disclaimer, the term of this patent is extended or adjusted under 35 U.S.C. 154(b) by 0 days.

(21) Appl. No.: 15/745,524

(22) PCT Filed: Jul. 14, 2016

(86) PCT No.: PCT/US2016/042197
§ 371 (c)(1),
(2) Date: Jan. 17, 2018

(87) PCT Pub. No.: WO2017/015039
PCT Pub. Date: Jan. 26, 2017

(65) Prior Publication Data
US 2018/0213791 A1 Aug. 2, 2018

(30) Foreign Application Priority Data
Jul. 17, 2015 (EP) .................................... 15177252

(51) Int. Cl.
*A01N 53/00* (2006.01)
*A01N 47/06* (2006.01)
*A01N 51/00* (2006.01)
*A01N 25/02* (2006.01)
*A01N 25/30* (2006.01)
*A01N 43/40* (2006.01)

(52) U.S. Cl.
CPC ............. *A01N 53/00* (2013.01); *A01N 25/02* (2013.01); *A01N 25/30* (2013.01); *A01N 43/40* (2013.01); *A01N 47/06* (2013.01); *A01N 51/00* (2013.01)

(58) Field of Classification Search
None
See application file for complete search history.

(56) References Cited

U.S. PATENT DOCUMENTS

| | | |
|---|---|---|
| 7,025,978 B1 | 4/2006 | Sirinyan et al. |
| 7,384,938 B2 | 6/2008 | Sirinyan et al. |
| 7,728,011 B2 | 6/2010 | Sirinyan et al. |
| 8,071,116 B2 | 12/2011 | Sirinyan et al. |
| 8,097,603 B2 | 1/2012 | Sirinyan et al. |
| 2006/0211655 A1 | 9/2006 | Mencke et al. |
| 2007/0020304 A1* | 1/2007 | Tamarkin ............... A01N 25/16 424/405 |
| 2008/0033017 A1 | 2/2008 | Arther |
| 2015/0038537 A1 | 2/2015 | Kalbe et al. |

FOREIGN PATENT DOCUMENTS

| | | |
|---|---|---|
| WO | 2014/131786 A1 | 9/2014 |
| WO | WO-2014131786 A1 * | 9/2014 ............ A01N 51/00 |

OTHER PUBLICATIONS

Bayer Healthcare LLC, Material Safety Data Sheet, Section 2: Composition/Information on Ingredients, May 18, 2010, retrieved from the Internet: http://www.bugspray.net/msds/advantage_2_msds.pdf, seven pages.
International Search Report for corresponding PCT/US2016/042197 dated Sep. 27, 2016, six pages.

* cited by examiner

*Primary Examiner* — Svetlana M Ivanova
(74) *Attorney, Agent, or Firm* — Rankin, Hill & Clark LLP

(57) ABSTRACT

The invention relates to an improved composition for the control of parasites on animals, comprising comparably high amounts of active substances from the group of agonists of the nicotinergic acetylcholine receptors of insects (neonicotinoids) and from pyrethroids in a new and improved formulation comprising an aliphatic cyclic carbonate, an aromatic alcohol, sorbitan monolaurate (Span 20) and optionally additionally further active and/or auxiliary substances. In particular, the invention relates to the use of such compositions for the control of ectoparasites such as, in particular, lice, fleas, ticks, mosquitoes and sand flies in pets such as, in particular, in dogs and ferrets.

17 Claims, 2 Drawing Sheets

SPOT-ON ACTIVE SUBSTANCE FORMULATION

The invention relates to an improved composition for the control of parasites on animals, comprising comparably high amounts of active substances from the group of agonists of the nicotinergic acetylcholine receptors of insects (neonicotinoids) and from pyrethroids in a new and improved formulation comprising an aliphatic cyclic carbonate, an aromatic alcohol, sorbitan monolaurate (Span 20), and optionally additionally further active and/or auxiliary substances. In particular, the invention relates to the use of such compositions for the control of ectoparasites such as, in particular, fleas, ticks and sand flies in pets such as, in particular, in dogs and ferrets.

INTRODUCTION

Compositions for the control of parasites such as, in particular, ectoparasites, which are based on a combination of active substances from the group of agonists of the nicotinergic acetylcholine receptors of insects (neonicotinoids) and from pyrethroids are known from the prior art. The disadvantage of spot-on formulations on the basis of permethrin alone is the low activity against fleas. Spot-on formulations based on agonists or antagonists of nicotinic acetylcholine receptors alone are highly active against fleas but have the disadvantage that they are ineffective against ticks. It has been described that insecticidal compositions on the basis of a combination of neonicotinoids and pyrethroids requires the use of relatively large amounts of the active compounds to act effectively against parasitic insects such as ticks and fleas on animals. However, such compositions with high amounts of the active substances are known to cause undesired side-effects such as skin irritations.

Especially the international application WO 2004/064522 with its corresponding US 2006/211655 relates to arthropod-repelling agents, comprising a combination of a pyrethrin or pyrethroid with an agonist of the nicotinergic acetylcholine receptors of arthropods (neonicotinoids). Therein, examples of suitable pyrethroids comprise permethrin, which may be present in an amount of 15 to 75 wt.-%. Examples of neonicotinoids comprise imidacloprid, which may be present in amount of 1 to 25 wt.-%.

Further, the patent family of WO 2002/087338 with its equivalents DE 101 17 676 and U.S. Pat. No. 7,728,011 relates to a dermally applicable liquid formulation comprising a combination of 35 to 60 wt.-% permethrin (pyrethroids) and 2.5 to 12.5 wt.-% imidacloprid (neonicotinoid) in a formulation on the basis of N-methylpyrrolidone (NMP) as the solvent, which is present in amounts between 27.5 to 62.5 wt. %.

Further, WO 2014/131786 relates to veterinary compositions for dermal application comprising a combination of imidacloprid and permethrin in a formulation on the basis of Dimethyl sulfoxide (DMSO) as the solvent, which is present in amounts between 20 to 60 wt. %.

Further compositions comprising neonicotinoids and pyrethroids are known for example from the international application WO 2004/098290, which relates to a combination of a pyrethrin or a pyrethroid with neonicotinoids agents for controlling parasites on animals, wherein the preferred pyrethroid is flumethrin (a so-called type II pyrethroid) which may be combined with the neonicotinoid imidacloprid. Therein it is mentioned that the compositions may comprise the pyrethroids in an amount up to 20 wt.-%, however the specific formulations in the examples comprise less than 1 wt.-% of the pyrethroid compound.

WO 2002/43494 relates to a composition for combating parasites on animals, comprising a combination of a neonicotinoid and a pyrethroid as the active ingredients. The formulations may comprise solvents, which may be selected amongst others from cyclic carbonates and benzyl alcohol. The compositions may also comprise auxiliary substances, comprising for example sorbitan monostearate. A specific composition comprising a selection of cyclic carbonate, benzyl alcohol and sorbitan monolaurate (Span 20) as a solubilizer is not described therein.

DE 198 07 633 relates to similar formulations for combating parasites on animals comprising a neonicotinoid alone as the active ingredient. A specific composition comprising a selection of cyclic carbonate, benzyl alcohol and sorbitan monolaurate (Span 20) as a solubilizer is not described therein. The problem arising from compositions with high amounts of active substances are the poor solubility of the actives, which are not readily dissolvable in any solvent or solvent formulation.

Imidacloprid is a protic active substance, whereas pyrethroids, such as in particular permethrin, are strongly aprotic compounds, which leads to the difficulty of finding a suitable solvent system for dissolving both components in high amounts and thus provide a homogenous and stable dermally applicable liquid formulation. A further difficulty arises from the tendency of the active substances to recrystallize and precipitate at room temperature and in particular at temperatures below room temperature. For preparing active substance compositions in the form of dermally applicable liquid formulations, it is thus necessary to prepare homogenous solutions or emulsions based on organic solvents. To achieve sufficient and stable dissolution of such high amounts of the active substances, in particular of imidacloprid and permethrin, so far high amounts of N-methylpyrrolidone (NMP) and dimethyl sulfoxide (DMSO) in amounts of at least 27.5 or 20 wt.-%, respectively, have been required.

However, N-methylpyrrolidone is on the list of Chemicals Known to the State to Cause Cancer or Reproductive Toxicity, cited in California Proposition 65 (1986). Although, DMSO is considered as non-toxic, it has the unusual and undesired property that many individuals perceive a unpleasing, garlic-like taste in the mouth and exhibit an undesired negative odor due to the sulphur component after contact with the skin. Further both, N-methylpyrrolidone and dimethyl sulfoxide are known to be less compatible and to cause undesired side-effects on the treated animals, such as e.g. the ability of DMSO to harm the eye. The most commonly reported side effects of NMP and DMSO include headaches and burning and itching on contact with the skin. Strong allergic reactions have also been reported. Further both, N-methylpyrrolidone and dimethyl sulfoxide are known to support transdermal passage of active substances. Therewith the active substances become partially systemic available and are topically not longer available. This reduces the efficacy of the topically active agents and is undesired in particular in spot-on or pour-on formulations.

In principle, alternative solvent formulations for active substance compositions, comprising combinations of neonicotinoids with pyrethroids have been described.

For example, the international application WO 2001/35739 relates to active substance compositions, comprising combinations of neonicotinoids such as imidacloprid with pyrethroids such as flumethrin using polysiloxanes containing quaternary amino groups as the auxiliary agents of the active substance formulations. Therein the active substances are present only in comparably small amounts.

The international application WO 2013/000572 with its corresponding US 2015/0038537 relates to a combination of an active substance from the group of pyrethroids such as deltamethrin or flumethrin (both so-called type II pyrethroids) with an active substance from the group of phenylpyrazoles such as fipronil. Therein a formulation comprising a propylene carbonate and benzylalcohol is mentioned. However, the application remains silent about a combination with a neonicotinoid and further relates to comparably small amounts of the pyrethroid of not more than 7 wt.-%.

The international application WO 2008/080542 and its priority application DE 10 2006 061538 relates to agents for controlling parasites on animals, comprising a combination of N-arylpyrazoles and pyrethroids in a formulation containing aliphatic cyclic carbonates and aliphatic cyclic or acyclic polyethers. Therein, a comparative example 3 is mentioned, comprising a combination of imidacloprid with the type II pyrethroid flumethrin in a small amount of less than 1 wt.-%.

OBJECT

It was the object of the present invention to find an alternative solvent or formulation for a highly effective active substance combination, particularly with a high level of long-term action, with high amounts of a neonicotinoid and a pyrethroid, such as preferably imidacloprid and permethrin, which avoids the aforementioned disadvantages. It was particularly desired to provide an alternative formulation for such highly concentrated active substance combination, which exhibits low toxic potential and causes less or even no undesired side-effects, in particular exhibits a high level of compatibility, particularly skin compatibility, and good applicability with low skin penetration (since the action of the active compounds should preferably be non-systemic). When searching for a solution for improving the compatibility of so far known active ingredient formulations, the inventors of the present invention have also considered to exchange NMP with its undesired toxic side-effects against DMSO, which is also a known and widely-used solvent. However, DMSO exhibits similar tissue penetration effects as NMP, thereby reducing the availability and efficacy of the topically applied actives by subcutaneous transport. Such effect is particularly not desired, and it was thus a further object of the present invention to develop a novel and improved active ingredient formulation for said specific active ingredient combination, which does not have the disadvantages of the known active ingredient formulations on the basis of NMP and DMSO, such as in particular the tissue penetration effects. At the same time the novel formulation should provide good solubility of the high amounts of active substances and thus allow the preparation of a homogeneously dissolved active substance composition with high stability (in particular storage-stability) in all climate zones. The novel compositions should particularly be suitable as spot-on or pour-on formulations.

DETAILED DESCRIPTION OF THE INVENTION

The inventors of the present invention surprisingly found that the aforementioned disadvantages can be solved by providing a composition for the control of parasites on animals, which comprises from about 2.5 to 12.5 wt.-% of at least one active substance selected from the group of agonists of the nicotinergic acetylcholine receptors of insects;

from about 30.0 to 60.0 wt.-% of at least one active substance, selected from the group of pyrethroids;

from about 8.0 to 48.0 wt.-% of an aliphatic cyclic carbonate;

from about 8.0 to 48.0 wt.-% of an aromatic alcohol;

sorbitan monolaurate (Span 20); as well as optionally at least one further active substance from the group of development inhibitors; and/or optionally additionally further active and/or auxiliary substances.

The group of agonists of the nicotinergic acetylcholine receptors of insects in the sense of the present invention preferably refers to neonicotinoids. Neonicotinoids are known for example from US 2006/0211655, U.S. Pat. No. 7,728,011 and from the prior art as mentioned therein. Examples comprise acetamiprid, clothianidin, dinotefuran, imidacloprid (also comprising imidacloprid analogues), nitenpyram, thiacloprid, and thiamethoxam, with imidacloprid (including imidacloprid analogues) being particularly preferred.

Imidacloprid ((E)-1-(6-chloro-3-pyridylmethyl)-N-nitroimidazolidin-2-ylideneamine or (2E)-1-[(6-chloro-3-pyridinyl)methyl]-N-nitro-2-imidazolidin-imine) is a synthetic insecticide having the structural formula

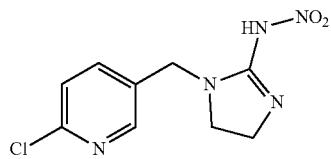 [SMILES: O=[N+]([O-])NC1=NCCN1Cc1ccc(Cl)nc1]

It acts as an insect neurotoxin and belongs to the class of neonicotinoids, which act on the central nervous system of insects by interfering with the transmission of stimuli in the insect nervous system. Specifically, it causes a blockage in the nicotinergic neuronal pathway, namely a blockage of the nicotinic acetylcholine receptors, thus preventing acetylcholine from transmitting impulses between nerves, resulting in the insect's paralysis, and even in its death. Imidacloprid is effective on contact and via stomach action.

Pyrethroids in the sense of the present invention are known for example from US 2006/0211655 and from the prior art as mentioned therein.

Within the context of the present invention, active substances from the group of the pyrethroids include both natural as well as synthetic pyrethroids. Natural pyrethroids include, in particular, pyrethrins, such as pyrethrin I and pyrethrin II as well as extracts thereof, as well as pyrethrum and derivatives thereof.

Synthetic pyrethroids may be classified as the so-called type I pyrethroids (without alpha-cyano group), type II pyrethroids (alpha-cyano pyrethroids with alpha-cyano group) and non-ester pyrethroids. They differ from one another substantially with regard to their acute actions.

In animal testing, type I pyrethroids lead to side effects such as the so-called "T-syndrome", which is named after the tremor that occurred in the test animals. Ataxia, hyperexcitability and hypersensitivity to stimuli are also observed in the case of the "T syndrome". Examples of type I pyrethroids comprise allethrin, bioallethrin, barthrin, cyclethrin, dimethrin, permethrin (indothrin), biopermethrin, phenothrin (sumithrin), resmethrin (cismethrin), bioresmethrin tetramethrin (phthalthrin) and transfluthrin.

Type II pyrethroids cause as a side effect the so-called "CS syndrome" which is named after the characteristic symptoms choreoathetosis (involuntary slow movements) and salivation that occurred in the test animals. In addition, a coarse tremor and colonic spasms also occur in this case. Examples of type II pyrethroids comprise alpha-cypermethrin, cyfluthrin, beta-cyfluthrin, cyhalothrin, cypermethrin, cyphenothrin, deltamethrin, fenpropanate, fenvalerate, flucythrinate, flumethrin, fluvalinate (tau-fluvalinate), tralomethrin and tralocythrin.

Examples of non-ester pyrethroids comprise, for example, etofenprox, halfenprox and silafluofen.

According to the present invention type I pyrethroids are preferred. Particularly preferred is permethrin.

Permethrin (3-phenoxybenzyl (1RS,3RS;1RS,3SR)-3-(2, 2-dichloro-vinyl)-2,2-dimethylcyclopropanecarboxylate or (3-phenoxyphenyl)methyl 3-(2,2-dichloroethenyl)-2,2-dimethylcyclopropanecarboxylate) is a synthetic insecticide, acaricide, and insect and acarid repellent having the structural formula

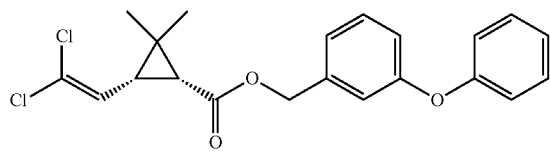 [SMILES: CC1(C)[C@H](C(=O)OCc2cccc(Oc3ccccc3)c2)[C@@H]1C=C(Cl)Cl]

It functions as a neurotoxin, affecting neuron membranes by prolonging sodium channel activation and acts against a broad spectrum by contact and stomach action. It exhibits a repellant effect.

Accordingly the composition of the present invention preferably comprises a combination of imidacloprid, as an active substance from the group of agonists of the nicotinergic acetylcholine receptors of insects (neonicotinoids), and permethrin, as an active substance from the group of the pyrethroids.

The compositions of the present invention may optionally comprise at least one further active substance, which may preferably be selected from the group of the so-called development inhibitors or insect growth regulators.

Development inhibitors or insect growth regulators regulate the development of insect larvae and prevent their further development and growth into an adult pest, and thus their reproduction. Development inhibitors may come, for example, from the group of the juvenile hormones. Development inhibitors and insect growth regulators include, for example, juvenile hormones, such as azadirachtin, diofenolan, fenoxycarb, hydroprene, kinoprene, methoprene, pyriproxyfen, tetrahydroazadirachtin, 4-chloro-2-(2-chloro-2-methylpropyl)-5-(6-iodo-3-pyridylmethoxy)pyridizin-3 (2h)-one; as well as chitin synthesis inhibitors, such as chlorofluazuron, cyromazine, diflubenzuron, fluazuron, flucycloxuron, flufenoxuron, hexaflumuron, lufenuron, tebufenozide, teflubenzuron, triflumuron. Pyriproxyfen and methoprene are preferred development inhibitors, particularly preferred is pyriproxyfen.

All of the active substances mentioned within the context of the invention can additionally be defined by the internationally known designations according to "The Pesticide Manual"; 10th edition, 1994, Ed. Clive Tomlin, Great Britain.

If applicable, the active substances used according to the invention can be present, depending on the type and arrangement of the substituents, in various stereoisomeric forms, particularly as enantiomers and racemates, wherein both the pure stereoisomers as well as mixtures thereof can be used according to the invention.

Optionally, the active substances according to the invention can also be used in the form of their salts, with pharmaceutically suitable acid addition salts and basic salts being eligible, such as, for example, salts of mineral acids or organic acids (for example carboxylic acids or sulphonic acids), such as, in particular, hydrochloric acid, sulphuric acid, acetic acid, glycolic acid, lactic acid, succinic acid, citric acid, tartaric acid, methanesulphonic acid, 4-toluene-sulphonic acid, galacturonic acid, gluconic acid, embonic acid, glutamic acid or aspartic acid. Pharmaceutically suitable basic salts include, for example, alkali metal salts, such as sodium or potassium salts, and alkaline earth metal salts, such as magnesium or calcium salts.

The active substances according to the invention can also be used in the form of their solvates, in particular hydrates, which includes both the solvates (in particular hydrates) of the active substances themselves as well as those of their salts.

The amounts of the active substances in the composition of the present invention may be varied broadly. Indicated amounts (e.g. in wt.-%) relate to the total weight of the composition.

According to the present invention the active substance from the group of agonists of the nicotinergic acetylcholine receptors of insects (neonicotinoids), such as in particular imidacloprid, may vary between about 2.5 to 12.5 wt.-%, preferably between about 5.0 to 10.0 wt.-%, more preferably between about 6.5 to 10.0 wt.-%.

According to the present invention the active substance from the group of pyrethroids, in particular type I pyrethroids such as in particular permethrin, may vary between about 30.0 to 60.0 wt.-%, preferably between about 32.0 to 60.0 wt.-%, more preferably between about 34.0 to 55.0 wt.-%.

In a preferred embodiment the composition of the present invention comprises the active substances from the group of agonists of the nicotinergic acetylcholine receptors of insects (neonicotinoids), such as in particular imidacloprid, and from the group of the pyrethroids, such as in particular a type I pyrethroid, particularly permethrin, in a total amount (sum) of at least 32.5 to 72.5 wt.-%, at least 37.0 to 70.0 wt.-%, at least 40.5 to 65.0 wt.-%, or at least 40.0 to 60.0 wt.-%.

In a further preferred embodiment the composition according to the present invention comprises the active substances from the group of agonists of the nicotinergic acetylcholine receptors of insects (neonicotinoids), such as in particular imidacloprid, and from the group of the pyrethroids, such as in particular a type I pyrethroid, particularly permethrin, in a (weight-) ratio of about 1:5.

As already mentioned above, in particular active substances from the group of the pyrethroids, such as inter alia permethrin, are known for their irritating effect on the skin and the mucosa and for the occurrence of side effects in the form of skin-incompatibility reactions, such as pruritus (itching), burning, pricking, erythema development and reddening, edema development and allergic reactions. In addition the occurrence of paresthesias has been described in connection with the application of pyrethroids, in particular with the application of type II pyrethroids (cyano-pyrethroids).

Further, undesired side-effects such as general symptoms of poisoning, headache, nausea, dizziness as well as disorders of the central nervous system, functional disorders of the liver and kidneys and blood count disorders can arise from the commonly used solvent N-methylpyrrolidone and DMSO. It is therefore preferred that the compositions of the present invention contain at a maximum equal to or less than (≤) 20.0 wt.-% N-methylpyrrolidone and/or DMSO, ≤10.0 wt.-% N-methylpyrrolidone and/or DMSO, preferably ≤ or <9.0 wt.-% N-methylpyrrolidone and/or DSMO, such as in particular 0 to 10.0 wt.-% or 0 to 9.0 wt.-% N-methylpyrrolidone and/or DMSO. In a very particularly preferred embodiment the compositions of the present invention are essentially free of N-methylpyrrolidone and DMSO.

However, as mentioned above, N-methylpyrrolidone has so far been required to sufficiently dissolve the high amounts of effective insecticidal combination products on the basis of e.g. imidacloprid and permethrin.

The inventors of the present invention have now surprisingly found that a solvent formulation comprising a mixture of one solvent selected from the group of aliphatic cyclic carbonates, preferably propylene carbonate, and of a second solvent selected from the group of aromatic alcohols, preferably benzyl alcohol, each in a specifically selected range, provides sufficient dissolution even of high amounts of the active substances according to the present invention.

Aliphatic cyclic carbonates in accordance with the present invention are also called carbonate ester, i.e. ester of carbonic acid and comprise for example ethylene carbonate, propylene carbonate and mixtures thereof, with propylene carbonate being preferred.

Aromatic alcohols comprise for example benzyl alcohol, phenylethanol, phenoxyethanol and mixtures thereof, with benzyl alcohol being preferred.

Accordingly it is particularly preferred to use a solvent mixture comprising propylene carbonate and benzylalcohol.

The amounts of the aliphatic cyclic carbonate and the aromatic alcohol in the composition of the present invention may be varied broadly. Indicated amounts (e.g. in wt.-%) relate to the total weight of the composition.

According to the present invention the aliphatic cyclic carbonate, such as in particular propylene carbonate, may vary between about 8.0 to 48.0 wt.-%, preferably between about 9.0 to 40.0 wt.-%, preferably between about 9.0 to 30.0 wt.-%. In a further preferred embodiment the propylene carbonate may vary between about 20.0 to 40.0 wt.-%, preferably between about 20.0 to 30.0 wt.-%.

According to the present invention the aromatic alcohol, such as in particular benzyl alcohol, may vary between about 9 to 40 wt.-%, preferably between about 9 to 30 wt.-%. In a further preferred embodiment the benzyl alcohol may vary between about 20.0 to 30.0 wt.-%.

According to the invention, any of the aforementioned ranges of the aliphatic cyclic carbonate may be combined with any of the aforementioned ranges of the aromatic alcohol.

It is particularly preferred that in the compositions according to the invention the cyclic carbonate, such as in particular propylene carbonate, and the aromatic alcohol, such as in particular benzyl alcohol, are present in a ratio of about 1:6 to 6:1, preferably about 1:5 to 5:1, preferably about 1:4 to 4:1, preferably about 1:3 to 3:1, preferably about 1:2.5 to 2.5:1. In most preferred embodiments of the compositions according to the invention the cyclic carbonate, such as in particular propylene carbonate, and the aromatic alcohol, such as in particular benzyl alcohol, are present in a ratio of about 1:2 to 2:1, preferably about 1:1.5 to 1.5:1, preferably about 1:1.2 to 1.2:1, preferably about 1:1.

In one embodiment the amount of aliphatic cyclic carbonate, such as in particular propylene carbonate, exceeds the amount of the aromatic alcohol, such as in particular benzyl alcohol or is at least substantially equal, resulting in preferred ratios of aliphatic cyclic carbonate:aromatic alcohol of about 6:1, preferably about 5:1, preferably about 4:1, preferably about 3:1, preferably about 2.5:1, and more preferably about 2:1, more preferably about 1.5:1, more preferably about 1.2:1, more preferred about 1:1.

Therein, the term "substantially equal" or "about" means to include a variance of ±5%.

The inventors of the present invention further surprisingly found that it is advantageous for the solubility and stability of the formulations to add sorbitan monolaurate (Span 20; E493) as a solubilizer to the high concentrated active ingredient composition of the present invention. By adding sorbitan monolaurate (Span 20) as a solubilizer to the formulation of the present invention the solubility of the high amounts of the active substances of the group of nicotinergic acetylcholine receptors of insects (neonicotinoids), in particular imidacloprid and of the group of the pyrethroid compounds, such as in particular the type I pyrethroids such as particularly permethrin, could be further improved remarkably. Surprisingly, the inventors in particular found that the crystallization and precipitation of said active substances for example at room temperature and even at temperatures below room temperatures such as in a refrigerator was decreased or even avoided. It was thus possible to further improve the stability and homogeneity of the compositions of the present invention by adding a solubilizer.

The particular suitability of Span 20 was in so far very surprising, as other common solubilizer, such as e.g. solubilizer from the group of sorbitan esters, such as for example sorbitan monooleate (Span 80), sorbitan monopalmitat (Span 40) or sorbitan tristearate (Span 65) did not achieve the desired effects sufficiently.

The improvement of solubility and homogeneity of the high concentrated active substance compositions of the present invention could be further enhanced by adding as an auxiliary substance a compound selected from the group of crystallization inhibitors such as for example glycerine, propylene glycol, mineral oils, silicon oils, vegetable oils, e.g. olive oil, rapeseed oil, soy bean oil, sunflower oil, cottonseed oil, peanut oil, linseed oil, rice bran oils etc. Preferred crystallization inhibitors are glycerine and propylene glycol as well as one or more vegetable oils, with glycerine being particularly preferred.

The combination of Span 20 with glycerine, propylene glycol or a vegetable oil as a crystallization inhibitor turned out to be very effective in increasing the solubility, stability and homogeneity of the high concentrated active ingredient formulations of the present invention.

The Span 20 may be present in the compositions of the present invention in amounts up to about 15.0 wt.-%, up to about 10.0 wt.-%, up to about 5.0 wt.-%, up to about 4.0 wt.-%, or up to about 3.0 wt.-%. The Span 20 can be present in the compositions of the present invention in an amount of at least about 0.01 wt.-%, at least about 0.05 wt.-%, at least about 0.1 wt.-%, at least about 0.2 wt.-%, at least about 0.3 wt.-%, at least about 0.4 wt.-%, at least about 0.5 wt.-%, at least about 1.0 wt.-%, at least about 1.5 wt.-%, at least about 2.0 wt.-%, at least about 2.5 wt.-%, at least about 3.0 wt.-%, more preferably at least about 3.5 wt.-%, at least about 4.0 wt.-%, at least about 4.5 wt.-%, at least about 5.0 wt.-%.

Preferably Span 20 is present in the compositions of the present invention in amounts ranging between about 3.0 to 15.0 wt.-%, about 3.5 to 15.0 wt.-%, about 4.0 to 15.0 wt.-%, about 4.5 to 15.0 wt.-%, about 5.0 to 15.0 wt.-%.

By combining the selected solvents as defined above with Span 20 in a new formulation for the selected active substance combination as defined above, it was surprisingly possible to provide a new active substance formulation which is not only highly effective in controlling parasites on animals, but which is particularly characterized by a remarkably improved compatibility, reduced undesired side-effects, such as mentioned above, reduced toxicity, improved applicability when applied topically (dermal, external application) and which is even improved with respect to its efficacy compared to common formulations with high amounts of N-methylpyrrolidone or DMSO, as the effect of transdermal active substance transport, effected e.g. by the NMP and DMSO, is reduced or even totally avoided.

The compositions of the present invention may optionally additionally comprise further active and/or auxiliary substances.

Suitable auxiliary substances are customary auxiliary substances, such as, for example, (additional) solvents, spreading agents, (additional) solubilizer, other than sorbitan monolaurate (Span 20), emulsifier, synergists for the active substances according to the invention, antioxidants, preservatives, stabilizers, pH-adjusting agents, thickeners, fillers, adherents, crystallization inhibitors, colorants, fragrances etc. Some compounds exhibit more than one auxiliary effect and may thus be classified in several groups of mentioned auxiliaries. Accordingly, some compounds may be mentioned in different groups.

Spreading agents (or further solubilizer) include, for example, surface active agents, such as surfactants, such as anionic surfactants (e.g. sodium laurylsulfate, fatty alcohol ether sulfates and monoethanolamine salts of mono-/di-alkylpolyglycolether orthophosphoric acid esters), cationic surfactants (e.g. cetyl trimethyl ammonium chloride) amphoteric surfactants (e.g. di-sodium-N-laurylaminodipropionate or lecithin), and non-ionic surfactants (e.g. polyoxyethylated castor oil, polyoxyethylated sorbitane monooleate, ethylalcohol, glycerol monosterate, polyoxyethylene stearate and alkylphenol polyglycol ether) as well as, in particular, polymeric surfactants, for example those based on polymethoxysiloxanes, silicones, fats and oils, such as, for example, silicone oils of different viscosities; fatty acid esters such as ethylstearate, di-n-butylester, lauric acid hexylester, dipropylene glycol pelargonate, esters of a branched fatty acid with a medium chain length and saturated $C_{16}$-$C_{18}$ fatty alcohols, isopropyl myristate, isopropyl palmitate, caprylic/capric acid esters from saturated fatty alcohols with a chain length of $C_{12}$-$C_{18}$, isopropyl stearate, oleic acid oleyl ester, oleic acid decyl ester, ethyloleate, lactic acid ethyl ester, wax-like fatty acid esters, dibutyl phthalate, adipic acid diisopropyl esters and ester mixtures; triglycerides based on oleic acid, palmitic acid, linoleic acid, stearic acid, caprylic acid and capric acid, such as in particular caprylic/capric acid triglyceride, triglyceride mixtures with vegetable fatty acids with a chain length of $C_8$-$C_{12}$ or other especially selected natural fatty acids, partial glyceride mixtures of saturated and unsaturated fatty acids and mono and/or diglycerides of the $C_8$-/$C_{10}$-fatty acids; fatty alcohols, such as isotridecyl alcohol, 2-octyldodecanol, cetylstearyl alcohol and oleyl alcohol; fatty acids, such as oleic acid, palmitic acid, linoleic acid, stearic acid, caprylic acid and capric acid, lactones, such as butyrolactone; phospholipids and phosphatidylcholines etc. Fatty acid esters are particularly preferred spreading agents, with isopropyl myristate being selected with particular preference.

Possible (additional) solvents include, for example, water, pyrrolidones, such as pyrrolidone-2, N-methylpyrrolidone, N-octyl-, N-butylpyrrolidone, low-boiling alcohols, such as isopropanol, ethanol, higher alcohols, such as n-octyl alcohol, lanolin alcohol and n-butanol, cyclic and acyclic ketones, such as acetone, methyl ethyl ketone and cyclohexanone, glycols, such as ethylene glycol and propylene glycol, aliphatic cyclic or acyclic ethers, such as tetrahydrofurfuryl alcohol, diethylene glycol monoethyl ether, dipropylene glycol monopropyl ether and glycofurol, benzyl benzoate, vegetable or synthetic oils, dimethylformamide (DMF), and glycerine etc.

Antioxidants and stabilizers which may be mentioned are sulphites or metabisulphites, such as potassium metabisulphite; organic acids, such as citric acid, ascorbic acid, malic acid; phenols, butylhydroxytoluene (BHT), butylhydroxyanisole, vitamin E (tocopherols) and derivatives thereof, etc., vitamin E (tocopherols) and its derivatives and butylhydroxytoluene (BHT) being preferred antioxidants.

The amounts of antioxidant may be varied broadly in the range of 0 to 1.0 wt.-%, preferably 0 to 0.5 wt.-%, preferably the amounts of antioxidants are in the range of 0.05 to 0.25 wt-%, more preferably in the range of 0.05 to 0.15 wt.-%.

However, vitamin E and its derivatives may be used in even higher amounts such as in a quantity of 0 to ≥20.0 wt.-%. Preferably, vitamin E or its derivatives is used in amounts ≥3 wt.-% preferably ≥5.0 wt.-%, preferably ≥7.0 wt.-%, preferably ≥10.0 wt.-%. Moreover, it is further preferred to use vitamin E or its derivatives in an amount of ≥12.0 wt.-%, more preferably ≥15.0 wt.-%, more preferably ≥18.0 wt.-%, still more preferably ≥20.0 wt.-%.

Therein and within the context of the present invention, vitamin E derivatives in particular relate to glycosides, esters, salts and complexes of vitamin E. Esters of vitamin E include for example vitamin E nicotinate and vitamin E acetate (or tocopherol nicotinate or acetate or tocopheryl nicotinate or acetate, respectively). Therein, vitamin E acetate is particularly preferred.

The addition of vitamin E or its derivatives, in particular in the comparably high amounts as defined herein, is preferred with respect to the findings as described in US 2015/038537, wherein it has been shown that side effects and incompatibility reactions, which can be caused by the application or the dermal (topical, external) contact with active substances from the group of pyrethroids, can be reduced or suppressed by the simultaneous administration of vitamin E, particularly vitamin E acetate (tocopheryl acetate), in particular in the comparably high amounts as defined herein. In particular, topical or dermal side effects, such as pruritus (itching) and erythema development (reddening) as well as alopecia and also an increased salivation of the mucosa can be reduced by means of the combination of the pyrethroids with vitamin E (vitamin E acetate) according to the invention. Further, paresthesias can be reduced or suppressed. In particular, the immediate (concurrent, simultaneous) administration of the insecticidal active substances with vitamin E or vitamin E acetate in a combination preparation is preferred in the sense of a prophylactic treatment.

Colorants are all colorants approved for use on animals and which can be dissolved or suspended.

Adherents, filler and thickener are, for example, cellulose derivatives, such as carboxymethylcellulose, methylcellulose and other cellulose, starch derivatives, polyacrylates, natural polymers such as alginates, gum arabic, gelatin, polyvinylpyrrolidone, polyvinyl alcohol, copolymers of methyl vinyl ether and maleic anhydride, polyethylene glycols, waxes, colloidal silica, etc.

Emulsifier which may be mentioned are, for example, nonionic surfactants, e.g. polyethoxylated castor oil, polyethoxylated sorbitan monooleate, glycerol monostearate, polyoxyethyl stearate, alkylphenyl polyglycol ethers, etc.; ampholytic surfactants such as disodium N-lauryl-[beta]-iminodipropionate or lecithin; anionic surfactants, such as sodium lauryl sulphate, fatty alcohol ether sulphates, mono/dialkyl polyglycol ether orthophosphate monoethanolamine salt; cationic surfactants such as cetyltrimethylammonium chloride.

It is certainly possible to use mixtures of more than one of the aforementioned substances in the compositions of the present invention.

The compositions according to the invention are environmentally compatible and user-friendly due to the very low level of toxicity.

In a preferred embodiment the composition of the invention comprises at least one additional active and/or auxiliary substance, which is selected from the group consisting of antioxidants, such as butylated hydroxytoluene (BHT), vitamin E or derivatives thereof, at least one crystallization inhibitor, such as glycerine, propylene glycol and/or at least one vegetable oil, organic solvents and water.

The compositions according to the invention are suitable for the control of parasitic insects that occur in the keeping and breeding of animals in pets and useful animals, as well as in zoo animals, laboratory animals, test animals and hobby animals. They are effective particularly against parasitic pests selected from the group of the ectoparasites, such as insects and mites (e.g. lice, flies, fleas, sand flies, mosquitoes, ticks, mites, etc.), in particular including, for example:

from the order of the Anoplura, for example, *Haematopinus* spp., *Linognathus* spp., *Solenopotes* spp., *Pediculus* spp., *Pthirus* spp.;

from the order of the Mallophaga, for example, *Trimenopon* spp., *Menopon* spp., *Eomenacanthus* spp., *Menacanthus* spp., *Trichodectes* spp., *Felicola* spp., *Damalinea* spp., *Bovicola* spp;

from the order of the Diptera, suborder Brachycera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cordylobia* spp., *Cochliomyia* spp., *Crysomyia* spp., *Sarcophaga* spp., *Wohlfartia* spp., *Gasterophilus* spp., *Oesteromyia* spp., *Oedemagena* spp., *Hypoderma* spp., *Oestrus* spp., *Rhinoestrus* spp., *Melophagus* spp., *Hippobosca* spp;

from the order of the Diptera, suborder Nematocera, for example, *Culex* spp., *Aedes* spp., *Anopheles* spp., *Culicoides* spp., *Phlebotomus* spp., *Simulium* spp.;

from the order of the Siphonaptera, for example, *Ctenocephalides* spp., *Echidnophaga* spp., *Ceratophyllus* spp., *Pulex* spp.;

from the order of the Metastigmata, for example, *Hyalomma* spp., *Rhipicephalus* spp., *Boophilus* spp., *Amblyomma* spp., *Haemaphysalis* spp., *Dermacentor* spp., *Ixodes* spp., *Argas* spp., *Ornithodorus* spp., *Otobius* spp.;

from the order of the Mesostigmata, for example *Dermanyssus* spp., *Ornithonyssus* spp., *Pneumonyssus* spp.;

from the order of the Prostigmata, for example *Cheyletiella* spp., *Psorergates* spp., *Myobia* spp., *Demodex* spp., *Neotrombicula* spp.; from the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidocoptes* spp., *Cytodites* spp., *Laminosioptes* spp.

Particularly preferred, according to the invention, is the control of parasitic insects from the group of the ectoparasites, such as, in particular, lice, ticks, fleas, mosquitoes and sand flies.

Accordingly, a preferred embodiment relates to compositions according to the present invention for use in the prophylactic or acute treatment against ectoparasites, in particular against lice, ticks, fleas, mosquitoes and sand flies.

Within the context of the present invention, the term useful and breeding animals includes, for example, cattle, horses, sheep, pigs, goats, camels, water buffalo, donkeys, rabbits, fallow deer, reindeer, fur-bearing animals, such as, for example, mink, chinchilla, raccoon, birds, such as, for example, hens, geese, turkeys, ducks, etc.

According to the invention, the term hobby animals and pets, as well as laboratory and test animals includes, for example, mice, rats, guinea pigs, golden hamsters, dogs and ferrets as well as hedgehogs.

Preferably, the compositions according to the invention are provided for use in the treatment of dogs and ferrets.

In this case, application can take place both prophylactically and therapeutically, or for acute treatment.

Accordingly, another preferred embodiment relates to compositions according to the present invention for use in the prophylactic or acute treatment of dogs and ferrets.

According to the invention, application on the animal takes place directly or preferably in the form of suitable preparations, such as, in particular, the active substance formulations according to the invention.

A skin contact that is as good and extensive as possible is in this case advantageous for optimal action, in particular the repellent action of the pyrethroid active substances.

The use of the compositions according to the invention for the external, topical or dermal use is particularly preferred.

Suitable preparations therefore are solutions or concentrates for administration after dilution for use on the skin or in body cavities, infusion formulations, gels, emulsions and suspensions, semi-solid preparations, such as formulations in which the active substance is processed in an ointment base or in an oil-in-water or water-in-oil emulsion base, solid preparations such as powders, premixes or concentrates, granulates, pellets, aerosols and active substance-containing molded bodies, which are used, for example, by dissolving and optionally diluting them for use on the skin etc. According to the invention, application preferably takes place by spraying, pouring, dripping or by application via collars for cats or dogs or ferrets.

In particular, the use as a spot-on or pour-on formulation is preferred according to the invention. Accordingly, the compositions of the present invention are preferably in the form of a spot-on formulation or a pour-on formulation.

The application volumes of the compositions of the present invention preferably vary between 0.075 to 0.25 ml/1.0 kg body weight of the animal treated, preferably 0.1 to 0.15 ml/1.0 kg body weight of the animal treated. Such small applicable volumes are particularly preferred for spot-on formulations, which are preferred according to the invention.

According to the invention, the use of the above-described novel compounds for the control of parasites, such as, in particular, ectoparasites, particularly of ticks, fleas and sand flies, for example by application on and treatment of equipment from the keeping of animals, such as, for example, animal baskets, padding, brushes, cages, stables, etc., is comprised. In this case, the use may also take place both for the prophylactic as well as for the acute treatment.

Accordingly, the invention further relates to a method of controlling ectoparasites, as defined above, on animals, the method comprising topically applying a composition according to the present invention to an animal, as defined above, to be treated. In such method the definitions and preferences as given above apply accordingly.

To prepare the compositions according to the invention, appropriate amounts of the desired components are mixed with one another in accordance with known methods using, for example, conventional stirring tanks or other suitable devices, preferably under heating the mixture prior to and upon mixing.

The invention is illustrated in more detail by the following examples. The examples merely constitute exemplifications, and the person skilled in the art is capable of extending the specific examples to other embodiments for which protection is sought.

EXAMPLES

Figure 1:
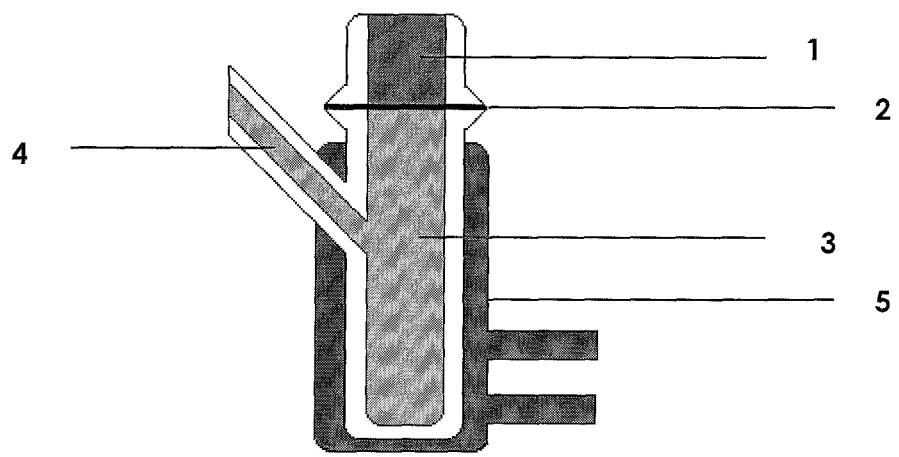
FIG. 1 illustrates a so-called Franz cell, wherein the references indicate:
(1) donor chamber
(2) skin sample
(3) acceptor chamber
(4) sampler tube
(5) water bath

1. Composition Examples (Compositions According to the Invention)

Example 1

Spot-on Formulation

| Ingredient | weight [g] | wt. [%] | mg/ml |
|---|---|---|---|
| Imidacloprid | 35 | 7 | 83.33 |
| Permethrin | 175.4 | 35.1 | 417.62 |
| Pyriproxyfen | 1.75 | 0.35 | 4.17 |
| Propylene carbonate | 132 | 26.6 | |
| Benzyl alcohol | 134 | 27 | |
| Span 20 | 17.7 | 3.6 | |
| BHT | 0.35 | 0.07 | 0.83 |
| total weight [g] | 496.2 | | |
| total volume [ml] | 420 | | |
| storage stability (RT) | | +++ | |
| storage stability refrigerator | | +++ | |

Example 2

Spot-on Formulation

| Ingredient | weight [g] | wt. [%] | mg/ml |
|---|---|---|---|
| Imidacloprid | 35.1 | 7.59 | 81.63 |
| Permethrin | 175.9 | 38.03 | 409.07 |
| Pyriproxyfen | 1.8 | 0.39 | 4.19 |
| Propylene carbonate | 100 | 21.62 | |
| Benzyl alcohol | 100 | 21.62 | |
| BHT | 0.35 | 0.08 | 0.81 |
| NMP | 39 | 8.43 | |
| Span 20 | 30.32 | 2.23 | |
| total weight [g] | 462.47 | | |
| total volume [ml] | 430 | | |
| storage stability (RT) | | +++ | |
| storage stability refrigerator | | +++ | |

The preparation of the compositions took place in each case by mixing the individual constituents with one another under slight heating, until a clear, single-phase liquid was obtained.

The Example compositions were stable at room temperature (RT) as well as under decreased temperatures in a refrigerator (5° C.+/−3° C.).

The stability of the Example compositions was examined with respect to the dissolution behaviour of the incorporated ingredients, the homogeneity of the prepared solutions, the (undesired) crystallization behavior and the occurrence of undesired discoloration.

The Example compositions were ranged with respect to these properties by "+++" (indicating excellent stability), "++" (indicating good stability), "+" (indicating low but still acceptable stability), "−" (indicating low and insufficient stability), "− −" (indicating worse and unacceptable stability) and "− − −" (indicating absolutely unsuitable compositions).

TABLE 1

Further Examples

| Ingredient [wt.-%] | Example 3-1 | Example 3-2 | Example 3-3 | Example 4-1 | Example 4-2 | Example 5 | Example 6 |
|---|---|---|---|---|---|---|---|
| Imidacloprid | 6.63 | 6.67 | 6.57 | 6.67 | 6.53 | 7.19 | 7.17 |
| Permethrin | 33.71 | 33.44 | 32.95 | 33.44 | 32.72 | 36.03 | 35.93 |
| Propylene Carbonat | 27.06 | 24.74 | 22.54 | 24.74 | 22.84 | 35.25 | 18.97 |
| Benzyl Alcohol | 27.06 | 24.74 | 22.54 | 24.74 | 22.84 | 19.27 | 35.69 |
| Span20 | 5.04 | 10.01 | 15 | 5.00 | 4.90 | 1.82 | 1.81 |
| Pyriproxyfen | 0.34 | 0.33 | 0.33 | 0.33 | 0.33 | 0.36 | 0.36 |
| BHT | 0.07 | 0.07 | 0.07 | 0.07 | 0.07 | 0.07 | 0.07 |
| Tocopherol acetate | 0 | 0 | 0 | 5.00 | 9.79 | 0 | 0 |

TABLE 1-continued

Further Examples

| Ingredient [wt.-%] | Example 3-1 | Example 3-2 | Example 3-3 | Example 4-1 | Example 4-2 | Example 5 | Example 6 |
|---|---|---|---|---|---|---|---|
| storage stability (RT) | +++ | +++ | +++ | +++ | +++ | +++ | ++ |
| storage stability refrigerator | +++ | +++ | ++ | ++ | + | ++ | + |

TABLE 2

Comparative Examples

| Ingredient | Comparative Example 1 Solubilizer = Span 80 (sorbitan monooleate) | | | comparative Example 2 Solubilizer = Span 40 (sorbitan monoalmitate) | | | Comparative Example 3 Solubilizer = Span 65 (sorbitan tristearate) | | |
|---|---|---|---|---|---|---|---|---|---|
| Imidacloprid | 6.73 | 6.67 | 6.57 | 6.73 | 6.67 | 6.51 | 6.73 | cannot be | |
| Permethrin | 33.71 | 33.44 | 32.95 | 33.71 | 33.44 | 32.65 | 33.71 | prepared | |
| Propylene Carbonat | 27.06 | 24.74 | 22.54 | 27.06 | 24.74 | 22.79 | 27.06 | | |
| Benzyl Alcohol | 27.06 | 24.74 | 22.54 | 27.06 | 24.74 | 22.79 | 27.06 | | |
| Solubilizer | 5.04 | 10.01 | 15 | 5.04 | 10.01 | 14.87 | 5.04 | 10.01 | 14.87 |
| Pyriproxyfen | 0.34 | 0.33 | 0.33 | 0.34 | 0.33 | 0.33 | 0.34 | | |
| BHT | 0.07 | 0.07 | 0.07 | 0.07 | 0.07 | 0.07 | 0.07 | | |
| storage stability (RT) | + | + | + | – | – – | – – – | – – | | |
| storage stability refrigerator | + | – | – – | – – – | – – – | – – – | – – – | | |
| Remarks | no suitable application volume could be prepared | | | the formulation became solid when stored in the refrigerator | | | | | |

| Ingredient | comparative Example 4 Solubilizer = Span 60 (sorbitan monostearate) | | |
|---|---|---|---|
| Imidacloprid | 6.73 | 6.67 | 6.51 |
| Permethrin | 33.71 | 33.44 | 32.65 |
| Propylene Carbonat | 27.06 | 0 | 22.79 |
| Benzyl Alcohol | 27.06 | 0 | 22.79 |
| Solubilizer | 5.04 | 10.01 | 14.87 |
| Pyriproxyfen | 0.34 | 0.33 | 0.33 |
| BHT | 0.07 | 0.07 | 0.07 |
| storage stability (RT) | – – – | – – – | – – – |
| storage stability refrigerator | – – – | – – – | – – – |
| Remarks | | the formulation became solid during storage | |

2. Permeation Experiments (Franz-Cell-Diffusion Test)

2.1 Diffusion Tests

The in vitro examination of the permeation of a test compound through skin is carried out with the method of FRANZ (1975) using a so-called Franz diffusion cell (see FIG. 1). Said cell consists of two glass chambers which are arranged vertically. The chamber containing the test solution (donor chamber) is at the top and is separated from the lower glass chamber, the acceptor chamber, by the dermatomized animal skin. The test substance is applied onto the animal skin via the donor chamber. The active ingredients of the test substance can permeate through a diffusion area of approximately 1.76 cm$^2$ through the animal skin and are collected in the acceptor chamber in a 30% NMP-containing collector solution (the presence of NMP is necessary to allow dissolution and thus recovery of the active ingredients in the collector solution), which is continuously stirred (100 rpm). The acceptor chamber is heated to 34° C. with a water bath, so that the solution in the Franz cell has a temperature similar to the temperature at the skin surface (32° C.).

The diffusion test is carried out for comparing the permeation behavior of imidacloprid, as a reference substance, from a composition according to the present invention compared to compositions with similar active ingredient combination on the basis of NMP and DMSO in the form of the market products Advantix™ (Bayer) and Ataxxa (TAD Pharma, KRKA d.d. NOVO mesto).

TABLE 3

Application volume and corresponding concentrations of the active ingredient

|  | Advantix 0.5 ml | Ataxxa 0.5 ml | Example Composition 1 0.6 ml |
|---|---|---|---|
| Dose of Imidacloprid [mg]: | 50.00 | 50.00 | 50.00 |
| Dose of Permethrin [mg]: | 250.00 | 250.00 | 250.00 |
| Theoretical maximum concentration of imidacloprid in 12 ml Medium (30% NMP) | | | |
| Dose of Imidacloprid [mg/ml]: | 4.17 | 4.17 | 4.17 |

2.2 Test Procedure

The acceptor chamber is completely filled with 12 ml degassed 30% NMP solution. In the next step the prepared skin is applied onto the acceptor chamber with the epidermal side upwards, avoiding the inclusion of air bubbles.

The donor chamber is fixed and sealed onto the skin and after 30 minutes the test solution is applied.

From the acceptor chamber samples (400 µl) are taken at the following timepoints:

First sampling directly before application of the test substance. Subsequent sampling after 8 and 24 hours.

The samples are analyzed with respect to the amount of permeated imidacloprid as the reference active ingredient in the NMP solution in the acceptor chamber by using a HPLC method.

2.3 HPLC Analysis

| HPLC-system: | System 10 (Dionex) | Chromatographic system: | |
|---|---|---|---|
| | | 0 min-3 min = 0% B (isocratic) | |
| | | 3 min-10 min = 40% B (linear) | |
| | | 10 min-11 min = 60% B (linear) | |
| | | 11 min-32 min = 60% B (isocratic) | |
| | | 32 min-45 min = 100% B (linear) | |
| | | 45 min-50 min = 100% B (isocratic) | |
| | | 50 min-51 min = 0% B (linear) | |
| | | 51 min-60 min = 0% B (isocratic) | |
| Pump A: | HPG-3200SD (Dionex) | Total flow: | 1.0 ml/min. |
| Pump B: | | Inject.-vol.: | 10 µl |
| Autosampler: | ASI-100 T (Dionex) | Sample temperature: | ambient |
| Detector: | PDA-100 (Dionex) | Detection wavelength: | 270 nm |
| Column oven: | TCC-100 (Dionex) | Column temperature: | 40° C. |
| HPLC-column: | Symmetry C18 5 µm 150 × 4.6 mm, manufacturer: Waters Serial-no.: 02173717113834 Batch: 0217 | | |
| Eluents: | | | |
| Eluent A | 10% Acetonitrile, 90% Water, 0.1% Phosphoric acid 85% ig (V/V/V) | | |
| Eluent B | 90% Acetonitrile, 10% Water, 0.1% Phosphoric acid 85% ig (V/V/V) | | |
| Reference substance: | Imidacloprid | Assay [%]: | 99.9 |

| theoretical Assay correction | practical Assay correction |
|---|---|
| 10.00 mg = 10.01 mg | 14.85 mg = 14.84 mg |
| 10.00 mg = 10.01 mg | 14.70 mg = 14.69 mg |

Remarks:

The initial weights were weighed out and diluted with ACN/H2O 8:2 to 10.0 ml in a volumetric flask (stock solution 1 and 2).

1.0 ml of each stock solution was diluted to 10.0 ml with ACN/H2O 1:1 in a volumetric flask. (reference solution 1 and 2)

Figure 2:
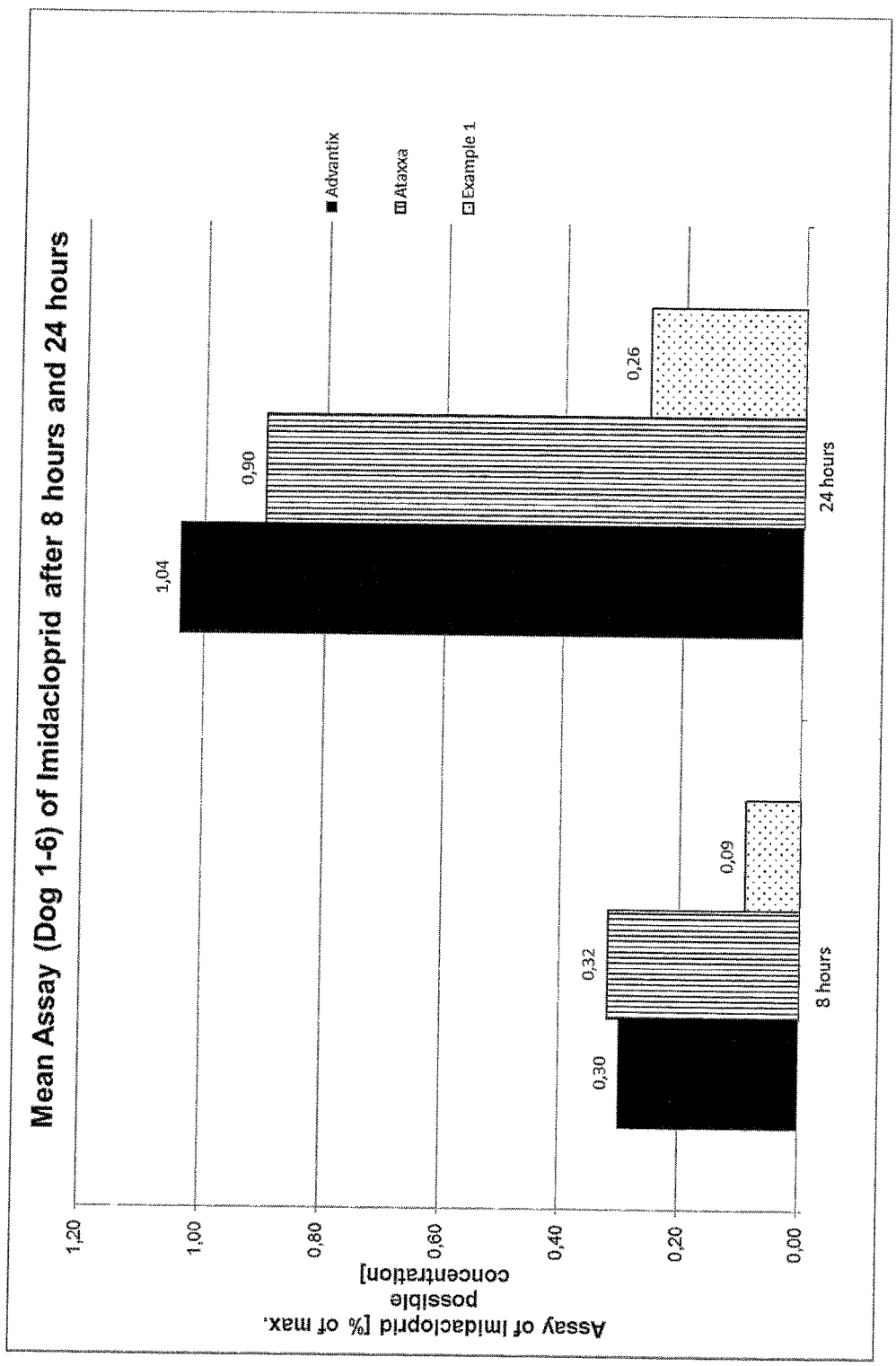
FIG. 2 shows the results of the Franz cell diffusion test for a composition according to Example 1 of the present invention compared to the products Advantix™ (Bayer) and Ataxxa (TAD Pharma, KRKA d.d. NOVO mesto).

The results are shown in FIG. 2. From the graph it becomes apparent that from the active ingredient formulations on the basis of NMP and DMSO significant amounts of the active ingredient imidacloprid penetrate through the animal skin, whereas the penetration is significantly reduced by using the new formulation according to the present invention. The reduced penetration is desired for the reasons set out above.

The invention claimed is:

1. A composition for the control of parasites on animals, comprising from about 2.5 to 12.5 wt.-% of at least one active substance selected from the group of agonists of the nicotinergic acetylcholine receptors of insects (neonicotinoids);

from about 30.0 to 60.0 wt.-% of at least one active substance, selected from the group of pyrethroids;

from about 8.0 to 48.0 wt.-% of an aliphatic cyclic carbonate;

from about 8.0 to 48.0 wt.-% of an aromatic alcohol; and sorbitan monolaurate, wherein said composition is essentially free of DMSO.

2. The composition according to claim 1, wherein the active substance from the group of agonists of the nicotinergic acetylcholine receptors of insects (neonicotinoids) is imidacloprid, and the active substance from the group of the pyrethroids is permethrin.

3. The composition according to claim 2, wherein the aliphatic cyclic carbonate is propylene carbonate and the aromatic alcohol is benzyl alcohol.

4. The composition according to claim 1, wherein at least one further active substance from the group of development inhibitors is present and is selected from the group consisting of pyriproxyfen and methoprene.

5. The composition according to claim 4, wherein the at least one further active substance from the group of development inhibitors is pyriproxyfen.

6. The composition according to claim 2, wherein at least one further active substance from the group of development inhibitors is present and is selected from the group consisting of pyriproxyfen and methoprene.

7. The composition according to claim 6, wherein the at least one further active substance from the group of development inhibitors is pyriproxyfen.

8. The composition according to claim 1, wherein the cyclic carbonate and the aromatic alcohol are present in a ratio of about 1:2 to 2:1.

9. The composition according to claim 2, wherein the cyclic carbonate and the aromatic alcohol are present in a ratio of about 1:2 to 2:1.

10. The composition according to claim 3, comprising
from about 5.0 to 10.0 wt.-% of the active substance from the group of agonists of the nicotinergic acetylcholine receptors of insects (neonicotinoids) and
from about 32.0 to 60.0 wt.-% of the active substance from the group of the pyrethroids.

11. The composition according to claim 3, comprising
from about 6.5 to 10.0 wt.-% of the active substance from the group of agonists of the nicotinergic acetylcholine receptors of insects (neonicotinoids) and
from about 34.0 to 55.0 wt.-% of the active substance from the group of the pyrethroids.

12. The composition according to claim 3, comprising
from about 5.0 to 10.0 wt.-% of the active substance from the group of agonists of the nicotinergic acetylcholine receptors of insects (neonicotinoids) and
from about 32.0 to 60.0 wt.-% of the active substance from the group of the pyrethroids.

13. The composition according to claim 6, comprising
from about 6.5 to 10.0 wt.-% of the active substance from the group of agonists of the nicotinergic acetylcholine receptors of insects (neonicotinoids) and
from about 34.0 to 55.0 wt.-% of the active substance from the group of the pyrethroids.

14. The composition according to claim 10, comprising from about 9.0 to 40.0 wt.-% of the aliphatic cyclic carbonate.

15. The composition according to claim 10, comprising from about 9.0 to 40.0 wt.-% of the aromatic alcohol.

16. The composition according to claim 15, comprising from about 9.0 to 40.0 wt.-% of the aromatic alcohol.

17. The composition according to claim 16, wherein at least one additional auxiliary substance is present and is selected from the group consisting of crystallization inhibitors, glycerine, propylene glycol and a vegetable oil.

* * * * *